United States Patent [19]

Manchand

[11] 4,115,650

[45] Sep. 19, 1978

[54] PROCESS FOR PREPARING 2,4-DIAMINO-5-(SUBSTITUTED BENZYL)-PYRIMIDINES

[75] Inventor: Percy Manchand, Montclair, N.J.

[73] Assignee: Hoffmann-La Roche Inc., Nutley, N.J.

[21] Appl. No.: 742,959

[22] Filed: Nov. 17, 1976

[51] Int. Cl.$^2$ .................. C07D 239/48; C07D 405/06
[52] U.S. Cl. ..................................... 544/324; 544/325
[58] Field of Search ............................... 260/256.4 N

[56] References Cited

U.S. PATENT DOCUMENTS 3,940,393  2/1976  Greenspan et al. .......... 260/256.4 N
3,992,379  11/1976  Liebenow et al. ........... 260/256.4 N

FOREIGN PATENT DOCUMENTS 2,363,533  6/1974  Fed. Rep. of Germany.

Primary Examiner—Paul M. Coughlan, Jr.
Attorney, Agent, or Firm—Samuel L. Welt; George M. Gould; William G. Isgro

[57] ABSTRACT 2,4-Diaminopyrimidines bearing a substituted benzyl group in position-1 are prepared from the correspondingly substituted α-alkoxymethylcinnamonitrile by treatment of the latter with an alkali metal alkoxide in mono-methyl ether of ethylene glycol and subsequently reacting the resulting reaction mixture with guanidine.

2 Claims, No Drawings

PROCESS FOR PREPARING 2,4-DIAMINO-5-(SUBSTITUTED BENZYL)-PYRIMIDINES

BRIEF SUMMARY OF THE INVENTION

The invention relates to a process for the preparation of 2,4-diaminopyrimidines characterized by the formula

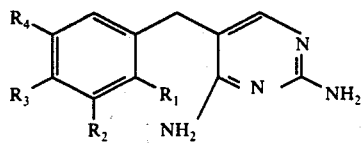

I wherein $R_1$ is hydrogen or lower alkyl; $R_2$ is hydrogen or lower alkoxy; $R_3$ is lower alkoxy or lower alkyl; $R_4$ is hydrogen or lower alkoxy; and $R_2$ and $R_3$, when taken together, are methylenedioxy,
can be exemplified as shown in Scheme I.

thoxy, ethoxy, propoxy, pentoxy, butoxy, heptoxy, and the like.

The process for preparing the diaminopyrimidines characterized by the formula

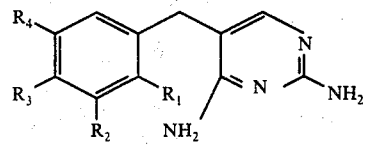

I wherein $R_1$ is hydrogen or lower alkyl; $R_2$ is hydrogen or lower alkoxy; $R_3$ is lower alkoxy or lower alkyl; $R_4$ is hydrogen or lower alkoxy; and $R_2$ and $R_3$, when taken together, are methylenedioxy,
can be exemplified as shown in Scheme I.

Scheme I

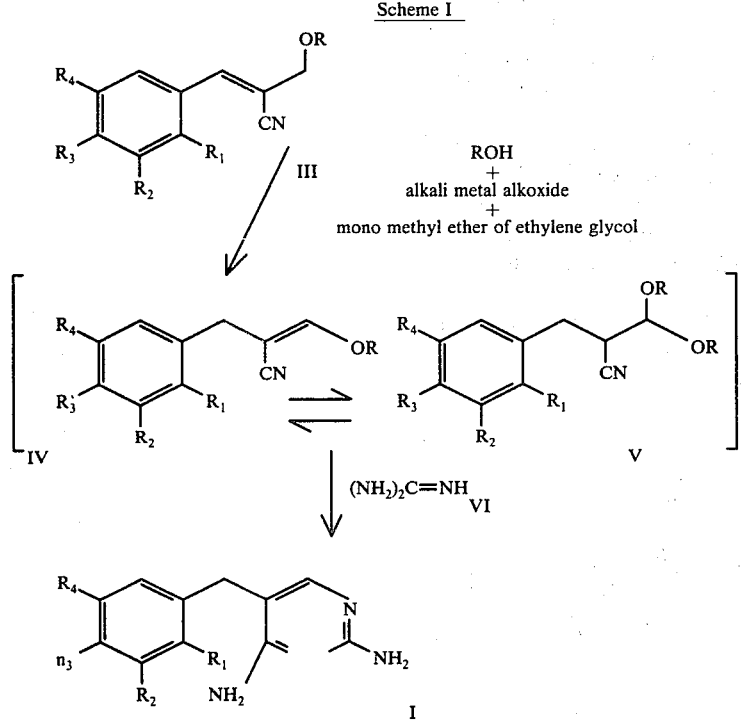

wherein $R_1$ is hydrogen or lower alkyl; $R_2$ is hydrogen or lower alkoxy; $R_3$ is lower alkoxy or lower alkyl; $R_4$ is hydrogen or lower alkoxy; and $R_2$ and $R_3$, when taken together, are methylenedioxy,
which comprises treating the correspondingly substituted α-alkoxymethylcinnamonitrile with an alkali metal alkoxide in mono-methyl ether of ethylene glycol and treating the resulting reaction mixture with guanidine. The end products are useful as potentiators of sulfonamides or as antibacterial agents.

DETAILED DESCRIPTION OF THE INVENTION

As used herein, the term "lower alkyl" denotes a hydrocarbon radical having from 1-7 carbon atoms, for example, methyl, ethyl, propyl, isopropyl, butyl, pentyl, hexyl, heptyl, and the like. The term "lower alkoxy" denotes a lower alkyl ether group in which the lower alkyl group is as described above, for example, mewherein $R_1$, $R_2$, $R_3$ and $R_4$ are as previously described and R is lower alkyl.

In Reaction Scheme I, the cinnamonitrile of formula III is converted to the reaction mixture comprising the enol ether of formula IV and the diacetal of formula V in the presence of an alkali metal alkoxide of 1 to 7 carbon atoms, such as potassium methoxide, sodium methoxide, sodium ethoxide and the like, most preferably in the presence of sodium methoxide, and an excess of an alkanol of the formula ROH wherein R is lower alkyl. The alkali metal alkoxide is preferably prepared fresh and in situ, i.e., by reacting an alkali metal with the desired alkanol of the formula ROH, exemplary of which are methanol, ethanol, propanol, and the like.

The conversion of the cinnamonitrile to the reaction mixture comprising the enol ether compound of formula IV and the diacetal compound of formula V is carried out in mono-methyl ether of ethylene glycol (also known as 2-methoxyethanol), which most preferably, is in the anhydrous state. The reaction temperature for the conversion is in the range of 50°–100° C; most preferably, the temperature is just below the reflux temperature of the reaction mixture. To complete the reaction, from about 1 to 6 hours are required. The cinnamonitrile of formula III is treated with the alkali metal alkoxide in a molar ratio which is in the range of from about one mole to about 4 moles per mole of cinnamonitrile of formula III utilized.

Upon the completion of the conversion of the cinnamonitrile of formula III to the enol ether of formula IV and diacetal of formula V, the reaction mixture, without separation of the compounds of formula IV and V, is treated with guanidine, at a temperature in the range of from about 100° to about 140° C. The guanidine is preferably, but not necessarily, generated in situ from the corresponding salt. A preferred salt comprises guanidine hydrochloride.

The conversion of the cinnamonitrile of formula III to the enol ether of formula IV and the diacetal of formula V and subsequent treatment thereof with guanidine is carried out under substantially anhydrous conditions.

The desired diaminopyrimidine of formula I can, thereafter, be recovered by known procedures, for example, by crystallization, extraction or the like.

The following are exemplary of the diaminopyrimidines of formula I which can be prepared by the process of the invention:

2,4-diamino-5-(3-methoxy-4,5-methylenedioxybenzyl)-pyrimidine;
2,4-diamino-5-(3,4,5-trimethoxybenzyl)-pyrimidine;
2,4-diamino-5-(3,4-dimethoxybenzyl)-pyrimidine;
2,4-diamino-5-(4-methoxybenzyl)-pyrimidine;
2,4-diamino-5-(4,5-dimethoxy-2-methylbenzyl)-pyrimidine; and
2,4-diamino-5-(3,5-dimethoxy-4-methylbenzyl)-pyrimidine.

The compounds of formula I are useful in combination with one or more sulfa drugs, such as, for example, $N^1$-(3,4-dimethyl-5-isoxazolyl)-sulfanilamide, 5-methyl-3-sulfanilamido-isoxazole, $N^1$-(2,6-dimethoxy-4-pyrimidinyl)-sulfanilamide, $N^4$-ethoxyacetyl-$N^1$-(5-methyl-3-isoxazolyl)-sulfanilamide, $N^1$-(4,5-dimethyl-3-isoxazolyl)sulfanilamide, $N^1$-(5,6-dimethoxy-4-pyrimidinyl)-sulfanilamide and the like as antibacterial agents. The addition of a compound of formula I to one of the above-mentioned sulfonamides results in a marked potentiation of the antibacterial activity of the sulfonamide. Thus, the compounds of formula I are useful as potentiators of sulfonamides.

The cinnamonitriles of formula III can be prepared according to known procedures. An exemplary reaction sequence is illustrated in Scheme II.

Scheme II

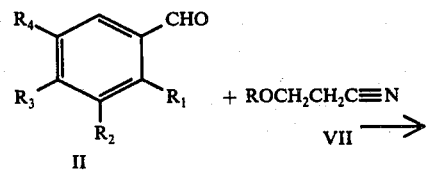

+ $ROCH_2CH_2C\equiv N$

VII ⟶

-continued

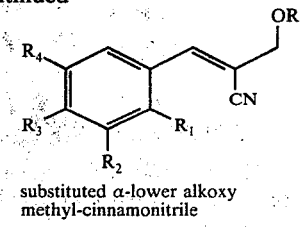

substituted α-lower alkoxy methyl-cinnamonitrile
III wherein R, $R_1$, $R_2$, $R_3$ and $R_4$ are as previously described.

The aldehydes of formula II are in the main known compounds. Those compounds which may be novel can readily be prepared by known techniques, for example, by the Vilsmeier reaction [Methoden der Organischen Chemie (HOUBEN WEYL) (1954): Volume: Sauerstoff Verbindungen II, Teil, 1, p. 29] or the like. Exemplary of such aldehydes are:

6-methylveratraldehyde;
3,4,5-trimethoxybenzaldehyde;
3,5-dimethoxy-4-methylbenzaldehyde;
3-methoxy-4,5-methylenedioxybenzaldehyde;
3,4-dimethoxybenzaldehyde; and the like.

The β-lower alkoxy propionitriles of formula VII are known compounds [C.A. 42, 521e (1948)].

The aldehyde of formula II is reacted with the β-lower alkoxy propionitrile of formula VII in the presence of an alkali metal lower alkoxide, such as sodium methoxide, sodium ethoxide, potassium methoxide, lithium methoxide, and the like and a lower alkanol of the formula ROH, wherein R is as previously described, such as methanol, ethanol, propanol, and the like. The reaction temperature is not critical, but is generally in the range of about 60° to about 140° C. The desired substituted α-lower alkoxymethyl-cinnamonitrile product can then be recovered by conventional techniques, for example, crystallization and the like. Exemplary of the substituted α-lower alkoxymethyl-cinnamonitriles of formula III are:

3-methoxy-4,5-methylenedioxy-α-methoxymethyl-cinnamonitrile;
3,4,5-trimethoxy-α-methoxymethyl-cinnamonitrile;
3,4-dimethoxy-α-methoxymethyl-cinnamonitrile;
3,5-dimethoxy-4-methyl-α-methoxymethyl-cinnamonitrile;
4,5-dimethoxy-2-methyl-α-methoxymethyl-cinnamonitrile; and the like.

The following Examples are illustrative of the invention. All temperatures are in degrees Centigrade, unless otherwise indicated.

EXAMPLE 1

Preparation of 3,4,5-trimethoxy-α-methoxymethyl-cinnamonitrile

To a 12 liter 3-necked round-bottomed flask equipped with a mechanical stirrer, thermometer, and condenser containing 3.5 liters of methanol was added 345.0 g. of clean sodium in small pieces and under an atmosphere of nitrogen. After all the sodium had reacted, the mixture was cooled to 35° and treated with 980 g. of 3,4,5-trimethoxybenzaldehyde and 595 g. of β-methoxypropionitrile. The mixture was stirred at room temperature for 20 hours, cooled to −10°, stirred at this temperature for 30 minutes and filtered. The product was washed with eight 2 liter portions, a total of 16 liters of water (until neutral), followed by 2 liters of cold (−10°) 80% methanol. The product was then dried in vacuo at room temperature for 20 hours (Note: a damp product will ruin the next step) to give 1.088 kg. (82.5%) of 3,4,5-trimethoxy-α-methoxymethyl-cinnamonitrile, mp 79°–81° as pale yellow crystals. Tlc. (SiO₂, ether-hexane 4:1, short UV): Rf 0.50.

EXAMPLE 2

Preparation of 2,4-diamino-5-(3,4,5-trimethoxybenzyl)-pyrimidine

To a 3-necked 2 liter round-bottomed flask equipped with a mechanical stirrer, thermometer and condenser was added 550 ml. of anhydrous methanol. 46.0 G. of clean sodium was added in small pieces under an atmosphere of argon; when the reaction was complete the mixture was cooled to 35° and treated with 254 ml. of anhydrous mono methyl ether of ethylene glycol (2-methoxyethanol) and 263 g. of 3,4,5-trimethoxy-α-methoxymethyl-cinnamonitrile. The mixture was stirred at 78°–80° for 5 hours, treated with 287.0 g. of guanidine hydrochloride and the condenser replaced with a Dean-Stark trap. The temperature was raised to 110° over a period of 30 minutes with the collection of methanol. After all the methanol was removed, stirring was continued at 110° for 30 minutes and the mixture evaporated in vacuo (aspirator) (about 100°) to give a dark brown semi-solid. To the hot solution (80°–90°) was added, with stirring, a mixture of 160 ml. of ethanol and 80 ml. of water. The stirred mixture was boiled under reflux for 30 minutes and then stirred at room temperature overnight, cooled to −10° and filtered. The product was washed with five 1 liter portions, a total of 5 liters of water until neutral (stirring with a spatula facilitates this process) followed successively with 250 ml., 175 ml. and 125 ml., a total of 550 ml. of cold (−10° to −15°) acetone. The product was dried in vacuo at 85° to give 215.5 g. (74.1%) of crude 2,4-diamino-5-(3,4,5-trimethoxybenzyl)-pyrimidine as off-white crystals, mp 197°–199°, a portion of which assayed 99.8%. Tlc. [SiO₂, CHCl₃(95),MeOH(15),N-H₄OH(2), short UV]. Thereafter, 106 g. of the preceding crude 2,4-diamino-5-(3,4,5-trimethoxybenzyl)-pyrimidine was heated with 600 ml. of 60% aqueous methanol and the hot solution filtered. The filtrate was stirred at room temperature for 1 hour, then at −10° for 15 minutes and filtered. The product was washed with 100 ml. of water and dried in vacuo at 85° to give 101.2 g. of 2,4-diamino-5-(3,4,5-trimethoxybenzyl)-pyrimidine as colorless crystals, mp 198°–199° which assayed 99.9%.

Calcd. for: $C_{14}H_{18}N_4O_3$: C, 57.92; H, 6.25; N, 19.30; Found: C, 58.06; H, 6.35; N, 19.46.

EXAMPLE 3

Preparation of 2,4-diamino-5-(4,5-dimethoxy-2-methylbenzyl)-pyrimidine

A 500 ml., 3-necked, round-bottomed flask equipped with a mechanical stirrer, thermometer, and condenser capped with a drying tube was charged with 60 ml. of methanol. 4.6 G. of clean sodium was added to the methanol. When all the sodium had reacted, the methanol was removed in vacuo at 45°, and 24.7 g. of 4,5-dimethoxy-2-methyl-α-methoxymethyl cinnamonitrile in 60.0 ml. of 2-methoxyethanol was added to the residue. The mixture was stirred at 90°–92° for 3 hours, treated with 28.6 g. of guanidine hydrochloride and boiled under reflux for 1.5 hours. The solvent was evaporated, first at atmospheric pressure and then in vacuo, and the residue treated with 250 ml. of water. The mixture was stirred at room temperature for 2 hours and the product collected by filtration. The product was washed with four 150 ml. portions, a total of 600 ml. of water, followed by four 40 ml. portions, a total of 160 ml. of cold (−15°) acetone, and then dried in vacuo at 80° overnight to give 20.6 g. (75%) of 2,4-diamino-5-(4,5-dimethoxy-2-methylbenzyl)-pyrimidine, mp 229°–231°.

EXAMPLE 4

Preparation of 2,4-diamino-5-(3,4-dimethoxybenzyl)-pyrimidine

A 1 liter, 3-necked, round-bottomed flask equipped with a mechanical stirrer, thermometer and condenser capped with a calcium sulfate drying tube was charged with 160 ml. of methanol. 18.4 G. of clean sodium was then added in small pieces under nitrogen. When all the sodium had reacted, 93.2 g. of 3,4-dimethoxy-α-methoxymethyl cinnamonitrile in 100 ml. of 2-methoxyethanol was added. The mixture was stirred at 90° for 4.0 hours and then treated with 114.8 g. of guanidine hydrochloride. The stirring was continued at 120° for 1.5 hours with the removal of methanol (Dean-Stark), followed by the complete removal of 2-methoxyethanol in vacuo. After cooling to 60°, the residue was treated with 64 ml. of ethanol and 32 ml. of water, stirred at 60° for 30 minutes, and cooled to −10°. The product was collected by filtration, washed with four 150 ml. portions, a total of 600 ml. of water, and then with two 100 ml. portions, a total of 200 ml. of cold (−15°) acetone. The mixture was then dried in vacuo overnight at 80° to give 80 g. (77%) of 2,4-diamino-5-(3,4-dimethoxybenzyl)-pyrimidine, mp 227°–231°.

The preceding sample of 2,4-diamino-5-(3,4-dimethoxybenzyl)-pyrimidine was heated at reflux in 200 ml. of dimethylformamide. The hot solution was filtered, the filtrate was stirred at room temperature for 1 hour and then at −5° for 30 minutes. The product was collected by filtration, washed with three 140 ml. portions, a total of 420 ml. of water, and dried in vacuo at 80° overnight to give 75.2 g. (73%) of 2,4-diamino-5-(3,4-dimethoxybenzyl)-pyrimidine, mp 230°–233°.

Analysis Calcd. for $C_{13}H_{16}N_4O_2$: C, 59.99; H, 6.20; N, 21.78; Found: C, 60.04; H, 6.29; N, 21.77.

I claim:

1. A process for the preparation of 2,4-diaminopyrimidines of the formula

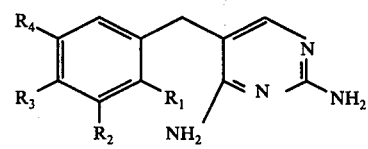

wherein $R_1$ is hydrogen or lower alkyl; $R_2$ is hydrogen or lower alkoxy; $R_3$ is lower alkoxy or lower alkyl; $R_4$ is hydrogen or lower alkoxy; and $R_2$ and $R_3$, when taken together, are methylenedioxy, which comprises the steps of treating the correspondingly substituted α-alkoxymethylcinnamonitrile with an alkali metal alkoxide in 2-methoxyethanol and an alkanol of the formula ROH, wherein R is lower alkyl, and treating the resulting reaction mixture with guanidine at a temperature in the range of from about 100° to about 140° C.

2. A process in accordance with claim 1, wherein the treatment of the substituted α-alkoxymethylcinnamonitrile with an alkali metal alkoxide is carried out at the reflux temperature of the reaction mixture.

* * * * *